United States Patent [19]
Reiffenrath et al.

[11] Patent Number: 5,744,058
[45] Date of Patent: Apr. 28, 1998

[54] DIENES AND LIQUID-CRYSTALLINE MEDIA

[75] Inventors: Volker Reiffenrath, Rossdorf; Bernhard Rieger, Münster, both of Germany

[73] Assignee: Merck Patent Gesellschaft Mit Beschrankter Haftung, Darmstadt, Germany

[21] Appl. No.: 458,704

[22] Filed: Jun. 2, 1995

[30] Foreign Application Priority Data

Jun. 3, 1994 [DE] Germany ............ 44 19 585.0

[51] Int. Cl.$^6$ ............ C09K 19/34; C09K 19/32; C09K 19/30; C09K 19/12
[52] U.S. Cl. ............ 252/299.61; 252/299.62; 252/299.63; 252/299.66; 252/299.67; 549/369; 549/370; 558/425; 558/411; 570/129; 544/298; 544/224; 546/339; 546/341; 560/1; 560/65; 560/63
[58] Field of Search ............ 252/299.66, 299.61, 252/299.63, 299.67, 299.62, 299.6; 570/129; 558/425.411; 568/647, 649, 651; 544/224, 298; 549/369, 370; 546/339, 341; 560/1, 65, 63

[56] References Cited

U.S. PATENT DOCUMENTS

| 5,047,169 | 9/1991 | Shibata et al. | 252/299.6 |
| 5,449,810 | 9/1995 | Fujita et al. | 558/425 |

*Primary Examiner*—C. H. Kelly
*Attorney, Agent, or Firm*—Millen, White, Zelano, & Branigan, P.C.

[57] ABSTRACT

Dienes of the formula I

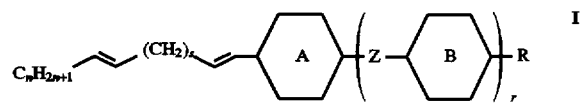

in which n is 0, 1, 2, 3, 4 or 5,
r is 1, 2 or 3,
s is 1 or 2,

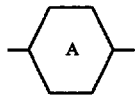

is trans-1,4-cyclohexylene or trans-1,3-dioxane-2,5-diyl,

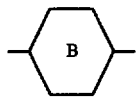

is trans-1,4-cyclohexylene, trans-1,3-dioxane-2,5-diyl, unfluorinated or mono- or polyfluorinated 1,4-phenylene, in which one or two CH groups may also be replaced by N, or the central part

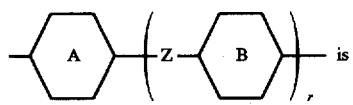

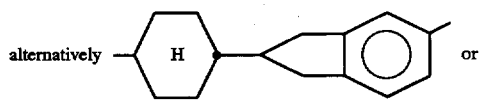

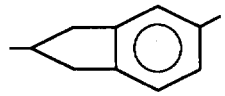

Z is a single bond, a bridging member selected from the group consisting of —CH$_2$CH$_2$—, —CH=CH—, —C≡C—, —CO—O—, —CH$_2$O—, —OCH$_2$— and —O—CO—, or any desired combination of two such bridging members, where two O atoms are not linked directly to one another, and R is —CN, —NCS, halogen or an alkyl, alkenyl, alkoxy or alkenyloxy group, in each case having up to 12 carbon atoms and in each case unsubstituted or monosubstituted or polysubstituted by fluorine and/or chlorine.

7 Claims, No Drawings

DIENES AND LIQUID-CRYSTALLINE MEDIA

The invention relates to dienes of the formula I,

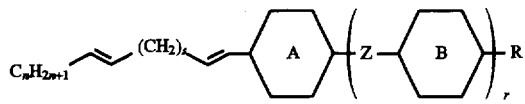

in which n is 0, 1, 2, 3, 4 or 5,
r is 1, 2 or 3,
s is 1 or 2,

is trans-1,4-cyclohexylene or trans-1,3-dioxane-2,5-diyl,

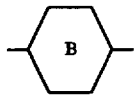

is trans-1,4-cyclohexylene, trans-1,3-dioxane-2,5-diyl, unfluorinated or mono- or polyfluorinated 1,4-phenylene, in which one or two CH groups may also be replaced by N, or the central part

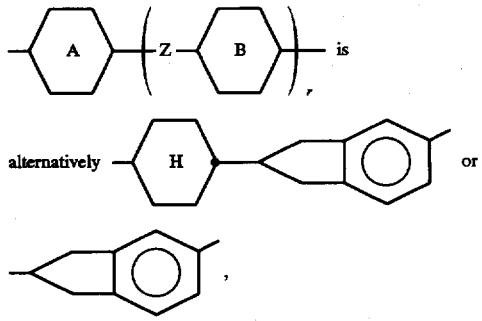

Z is a single bond, a bridging member selected from the group consisting of —CH$_2$CH$_2$—, —CH=CH—, —C≡C—, —CO—O—, —CH$_2$O—, —OCH$_2$— and —O—CO—, or any desired combination of two such bridging members, where two O atoms are not linked directly to one another, and R is —CN, —NCS, halogen or an alkyl, alkenyl, alkoxy or alkenyloxy group, in each case having up to 12 carbon atoms and in each case unsubstituted or monosubstituted or polysubstituted by fluorine and/or chlorine.

EP-A 0 122 389 discloses similar compounds, for example of the following formulae

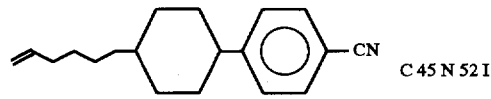

C 45 N 52 I

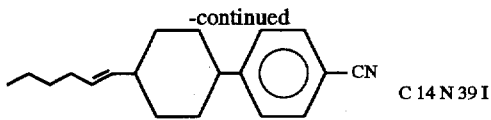

C 14 N 39 I

However, these compounds do not satisfy all requirements, in particular with respect to clearing points, for applications in STN displays.

Like similar compounds, for example those disclosed in DE-A 26 36 684 and EP-A 0 122 389, the compounds of the formula I can be used as components of liquid-crystalline media, in particular for displays based on the principle of the twisted cell.

All the substances employed hitherto for this purpose have certain disadvantages, for example excessively high melting points, excessively low clearing points, inadequate stability towards the action of heat, light or electric fields, excessively low electrical resistance, excessively high temperature dependence of the threshold voltage, and unfavourable dielectric and/or elastic properties.

The invention had the object of finding novel liquid-crystalline compounds which are suitable as components of liquid-crystalline media, in particular for nematic media having positive dielectric anisotropy, and which do not have the disadvantages of the known compounds, or only do so to a lesser extent. This object has been achieved by the provision of the novel compounds of the formula I.

It has been found that the compounds of the formula I are eminently suitable as components of liquid-crystalline media. In particular, they can be used to obtain liquid-crystalline media having broad nematic ranges, excellent nematogeneity down to low temperatures, good chemical stability, low temperature dependence of the threshold voltage and/or small optical anisotropy. In addition, the novel compounds have good solubility for other components of such media and high positive dielectric anisotropy at the same time as favourable rotational viscosity and excellent elastic properties. The compounds of the formula I make possible STN displays having a very steep electro-optical characteristic line and having short response times.

Compounds containing relatively long-chain radicals R (for example alkyl or alkoxy having 5–12 carbon atoms) are also suitable as components of ferroelectric smectic LC mixtures.

In the pure state, the compounds of the formula I are colourless and form liquid-crystalline mesophases in a temperature range which is favourably located for electro-optical use.

The invention thus relates to the compounds of the formula I and to the use of the compounds of the formula I as components of liquid-crystalline media, to liquid-crystalline media containing at least one compound of the formula I and to electro-optical displays containing such media.

Above and below, n, r, s,

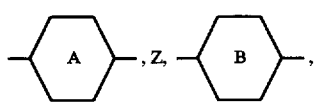

and R are as defined above, unless expressly stated otherwise.

In the compounds of the formula I, the alkyl groups $C_nH_{2n+1}$ are preferably straight-chain. Accordingly $C_nH_{2n+1}$ is preferably methyl, ethyl or n-propyl or likewise preferably H. n is preferably 0 or 1. s is preferably 2.

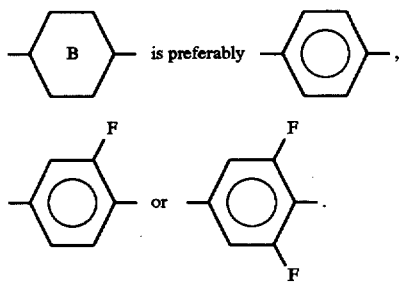

R is preferably CN, alkyl, F, Cl or fluorinated alkyl or alkoxy, particularly preferably —$OCH_2CF_3$, $OCHFCF_3$, —$CF_3$, —$OCHF_2$ or —$OCF_3$. Very particular preference is given to the compounds in which R=CN, r=1 and

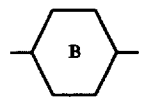

=1,4-phenylene.

r is preferably 1 or 2.

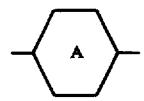

is preferably trans-1,4-cyclohexylene. Z is preferably a single bond.

Furthermore, the compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and suitable for said reactions. Use can also be made here of variants which are known per se, but are not described here in greater detail.

If desired, the starting materials can also be formed in situ, by not isolating them from the reaction mixture, but instead immediately converting them further into the compounds of the formula I.

Preferably, an aldehyde of the formula II

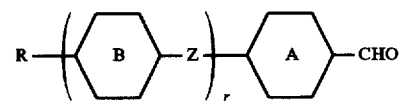

in which R,

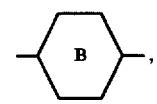

Z, r and

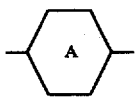

are as defined above, is reacted with an appropriate unsaturated phosphonium salt by the Wittig method to give a compound of the formula I, which is subjected to E/Z isomerization.

Some of the starting materials and their reactive derivatives are known, and some can be prepared without difficulties from compounds known from the literature by standard methods of organic chemistry. The precursors of the formula II suitable for the synthesis are obtainable, for example, by the following synthetic scheme:

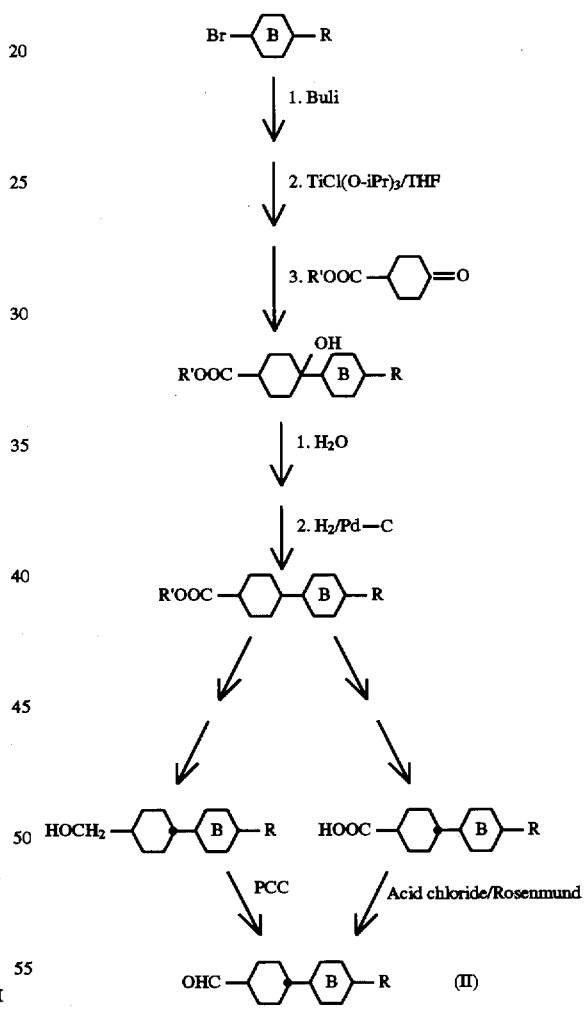

The Grignard compound obtained from the corresponding bromobenzene derivative is reacted with chlorotrialkyl orthotitanate or -zirconate by the method of WO 87/05599 to give the tertiary cyclohexanol. After elimination of water, hydrogenation of the double bond and isomerization, the trans-cyclohexanecarboxylate is obtained by conventional methods. The latter is converted into the suitable precursors of the formula II by conventional standard methods.

A further method of synthesizing tricyclic compounds is given, for example, in the following scheme:

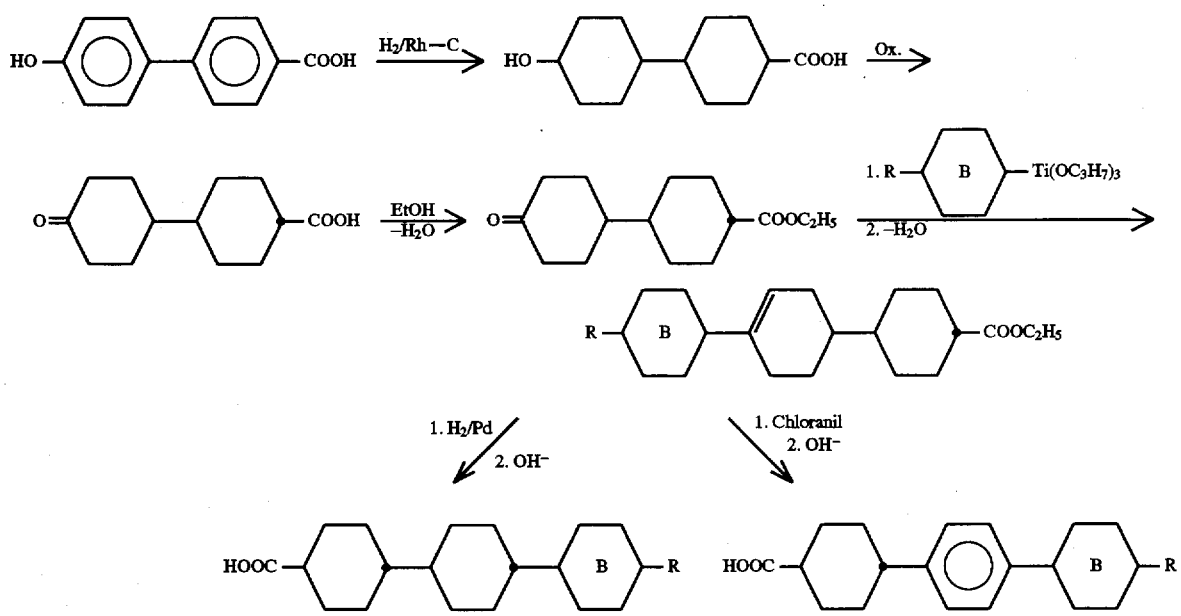

The compounds of the formula I containing lateral fluorine are obtained entirely analogously to the first synthetic scheme by using

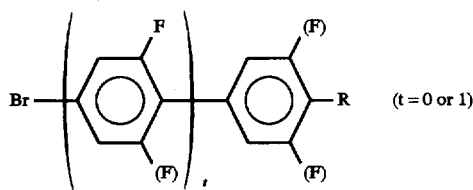

instead of the bromobenzene derivative. The bromobiphenyl compounds can be prepared in a manner known per se by transistion metal-catalysed coupling reactions (E. Poetsch, Kontakte (Darmstadt) 1988 (2), p. 15).

It is apparent to the person skilled in the art that the abovementioned synthetic methods can also be modified by carrying out the syntheses described with precursors in which the radical R has been replaced by a group which can be converted into R. For example, alkoxy compounds can be converted by ether cleavage into corresponding phenols, from which the OCF$_3$ and OCF$_2$H compounds can be prepared by routine methods by reaction with CCl$_4$/HF or CClF$_2$/NaOH. The corresponding benzoic acids can be converted into the nitrites or, by treatment with SF$_4$, the CF$_3$ compounds.

However, it frequently proves advantageous to react a phosphonium salt of the formula III

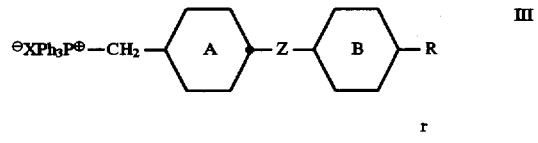

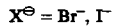

with an appropriate unsaturated aldehyde by the Wittig method. The compounds of the formula III are obtained from the cyclohexylmethyl alcohols described above by the following scheme:

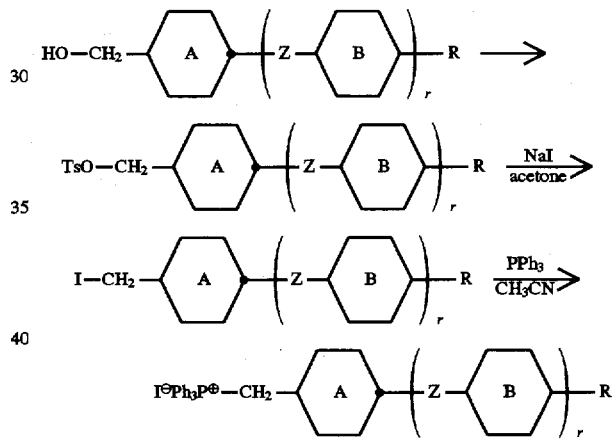

The alcohols can be converted by the Finkelstein method via the tosylates into the corresponding iodides, which are then converted into the corresponding phosphonium salts by boiling in acetonitrile containing PPh$_3$.

The ylides derived from these phosphonium salts (prepared by treatment with n-BuLi in hexane at −70° C. in the absence of oxygen) react with aldehydes to give preferentially the cis-olefins. These cis-olefins are then isomerized by the phosphorous betaine method of E. Vedejs and P. C. Fuchs (JACS 95,822, (1973)) or by treatment with sodium benzenesulfinate/1N hydrochloric acid to give the trans-olefins.

The liquid-crystalline media according to the is invention preferably contain 2 to 40, in particular 4 to 30, components as further constituents besides one or more compounds according to the invention. These media preferably contain 7 to 25 components besides one or more compounds according to the invention. These further constituents are preferably selected from nematic or nematogenic (monotropic or isotropic) substances, in particular substances from the classes of the biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes 1-cyclohexyl-2-biphenylylethanes, 1-phenyl-2-cyclohexylphenylethanes and tolans. The 1,4-phenylene groups in these compounds may also be fluorinated.

The most important compounds suitable as further constituents of media according to the invention can be characterized by the formulae 1, 2, 3, 4 and 5:

|  |  |
|---|---|
| R'-L-E-R" | 1 |
| R'-L-COO-E-R" | 2 |
| R'-L-OOC-E-R" | 3 |
| R'-L-CH$_2$CH$_2$-E-R" | 4 |
| R'-L-C≡C-E-R" | 5 |

In the formulae 1, 2, 3, 4 and 5, L and E, which may be identical or different, are in each case, independently of one another, a bivalent radical from the group formed by -Phe-, -Cyc-, -Phe—Phe-, -Phe-Cyc-, -Cyc—Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe—Phe-, -Phe-Cyc, -Cyc—Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc—Cyc-, -G-Phe- and -G-Cyc-.

Compounds of the sub-formulae 1a, 2a, 3a, 4a and 5a, are compounds of formulae 1, 2, 3, 4 and 5, where R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. Compounds of the sub-formulae 1b, 2b, 3b, 4b and 5b, are compounds of formulae 1, 2, 3, 4 and 5, where R" is —CN, —CF$_3$, —OCF$_3$, —OCHF$_2$, F, Cl or —NCS; in this case, R has the meaning given for the compounds of the sub-formulae 1a to 5a and is preferably alkyl or alkenyl. R" is particularly preferably selected from the group consisting of —F, Cl, CF$_3$, —OCHF$_2$ and —OCF$_3$. However, other variants of the proposed substituents in the compounds of the formulae 1, 2, 3, 4 and 5 are common. Many such substances or alternatively mixtures thereof can be obtained by methods which are known from the literature or analogous thereto.

Besides components from the group consisting of the compounds 1a, 2a, 3a, 4a and 5a (Group 1), the media according to the invention preferably also contain components from the group consisting of the compounds 1b, 2b, 3b, 4b and 5b (Group 2), whose proportions are preferably as follows:

Group 1: 20 to 90%, in particular 30 to 90%, Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed.

Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

The media according to the invention are particularly suitable for use in MLC displays.

In the present application and in the examples below, the structures of the liquid-crystal compounds are indicated by acronyms, the transformation into chemical formulae taking place in accordance with Tables A and B below. All radicals C$_n$H$_{2n+1}$ and C$_m$H$_{2m+1}$ are straight-chain alkyl radicals having n or m carbon atoms respectively. The coding in Table B is self-evident. In Table A, only the acronym for the parent structure is given. In individual cases, the acronym for the parent structure is followed, separated by a hyphen, by a code for the substituents R$^1$, R$^2$, L$^1$ and L$^2$:

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 44 19 585.0, are hereby incorporated by reference.

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nmF | $C_nH_{2n+1}$ | $C_mH_{2m+1}$ | F | H |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nNF | $C_nH_{2n+1}$ | CN | F | H |
| nAm | $C_nH_{2n+1}$ | $COOC_mH_{2m+1}$ | H | H |
| nF.Cl | $C_nH_{2n+1}$ | Cl | H | F |

TABLE A

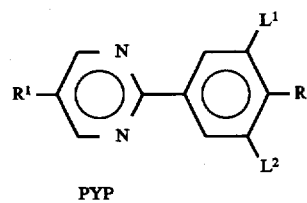

PYP

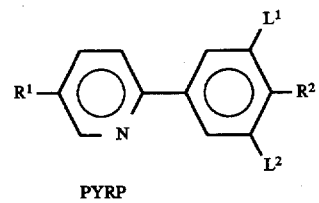

PYRP

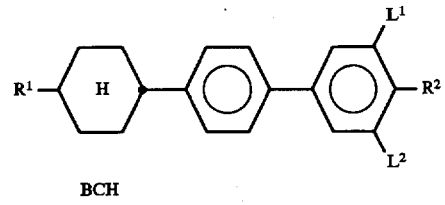

BCH

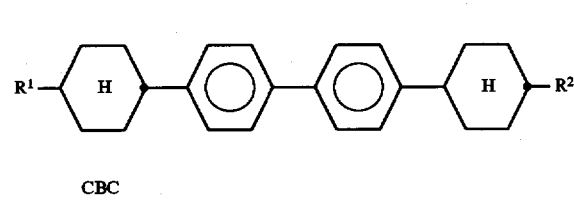

CBC

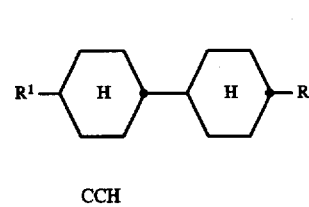

CCH

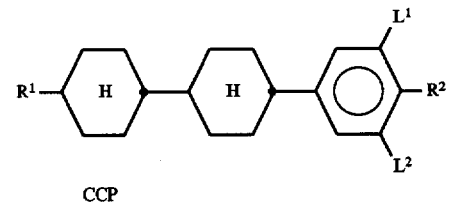

CCP

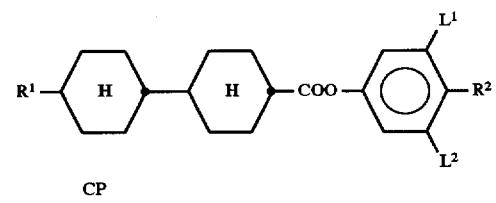

CP

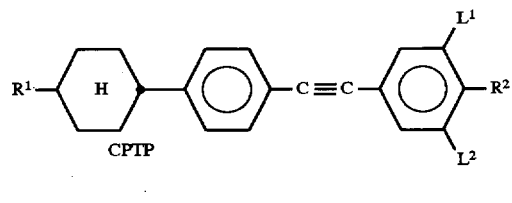

CPTP

TABLE A-continued
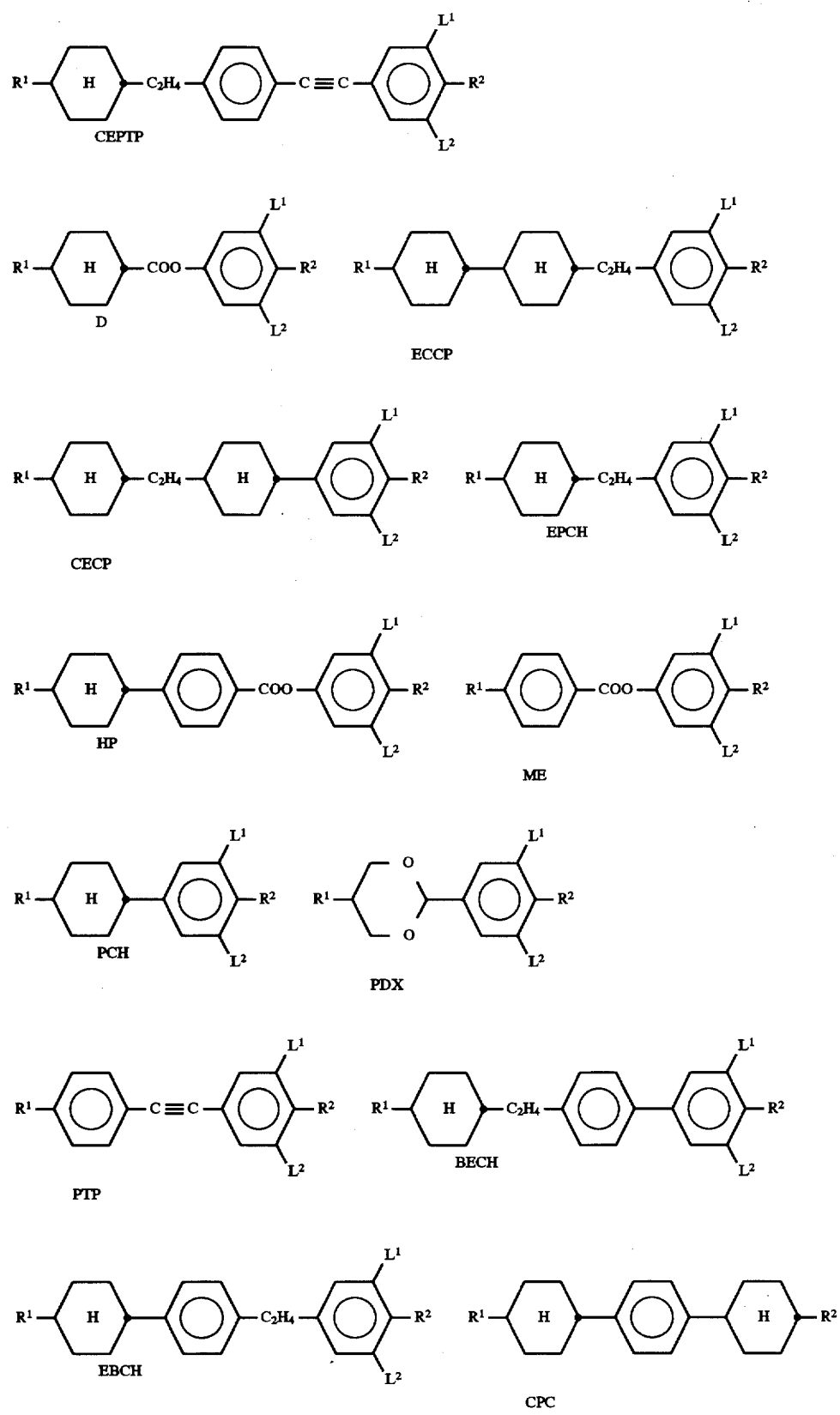

TABLE A-continued
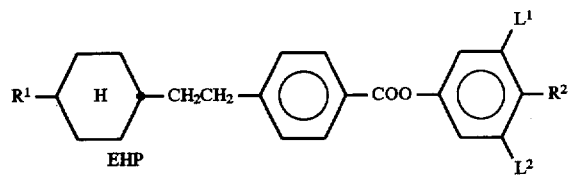
EHP
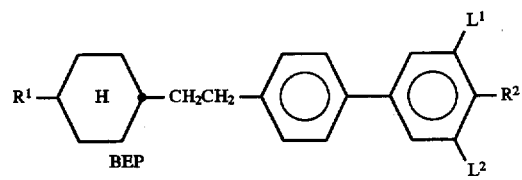
BEP
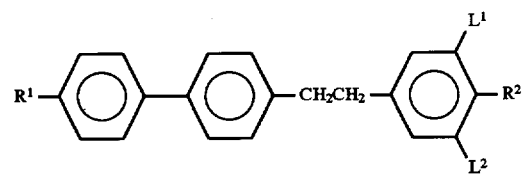
ET
TABLE B
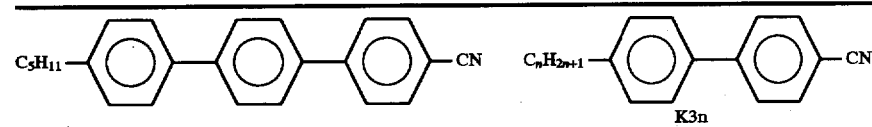
T15     K3n
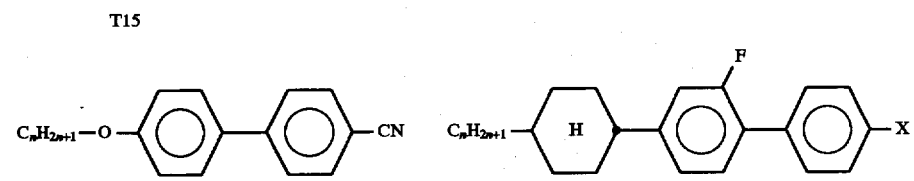
M3n     BCH-n.FX
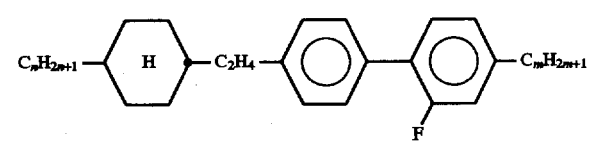
Inm
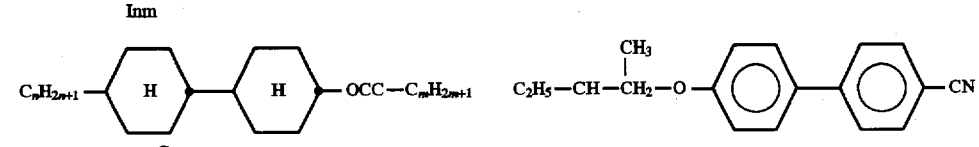
C-nm     C15
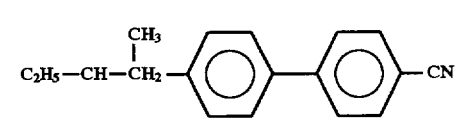
CB15

TABLE B-continued
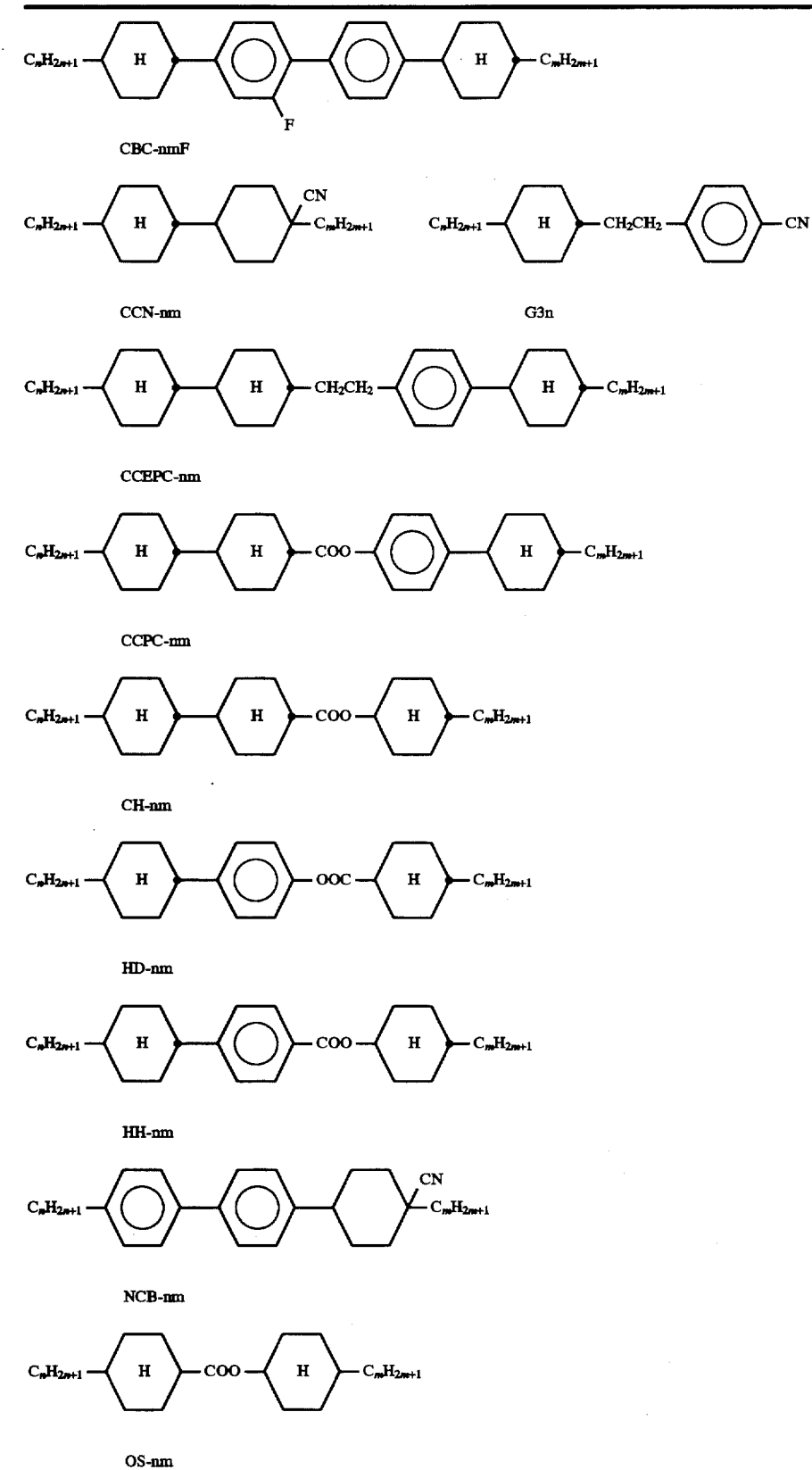

TABLE B-continued
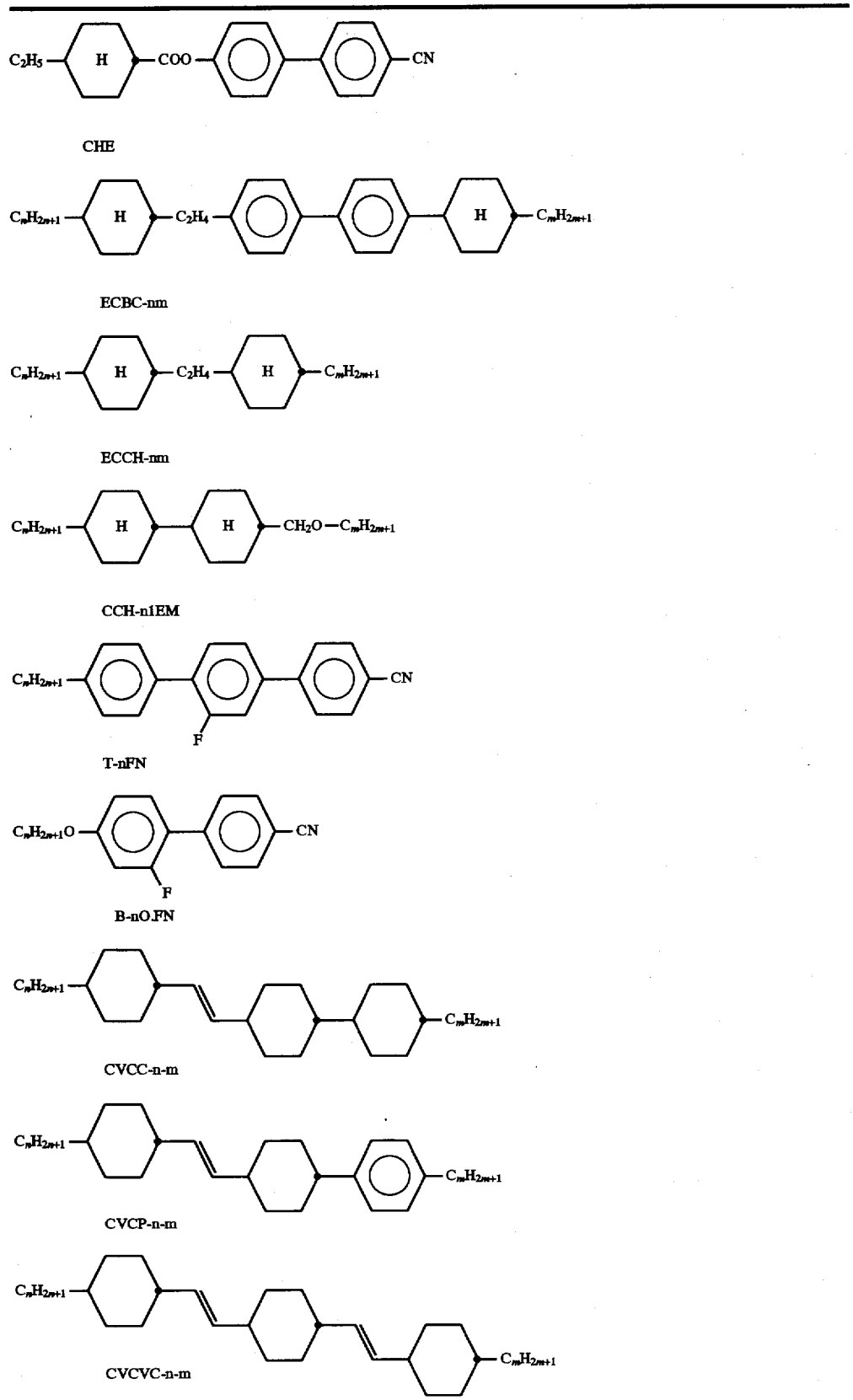

TABLE B-continued

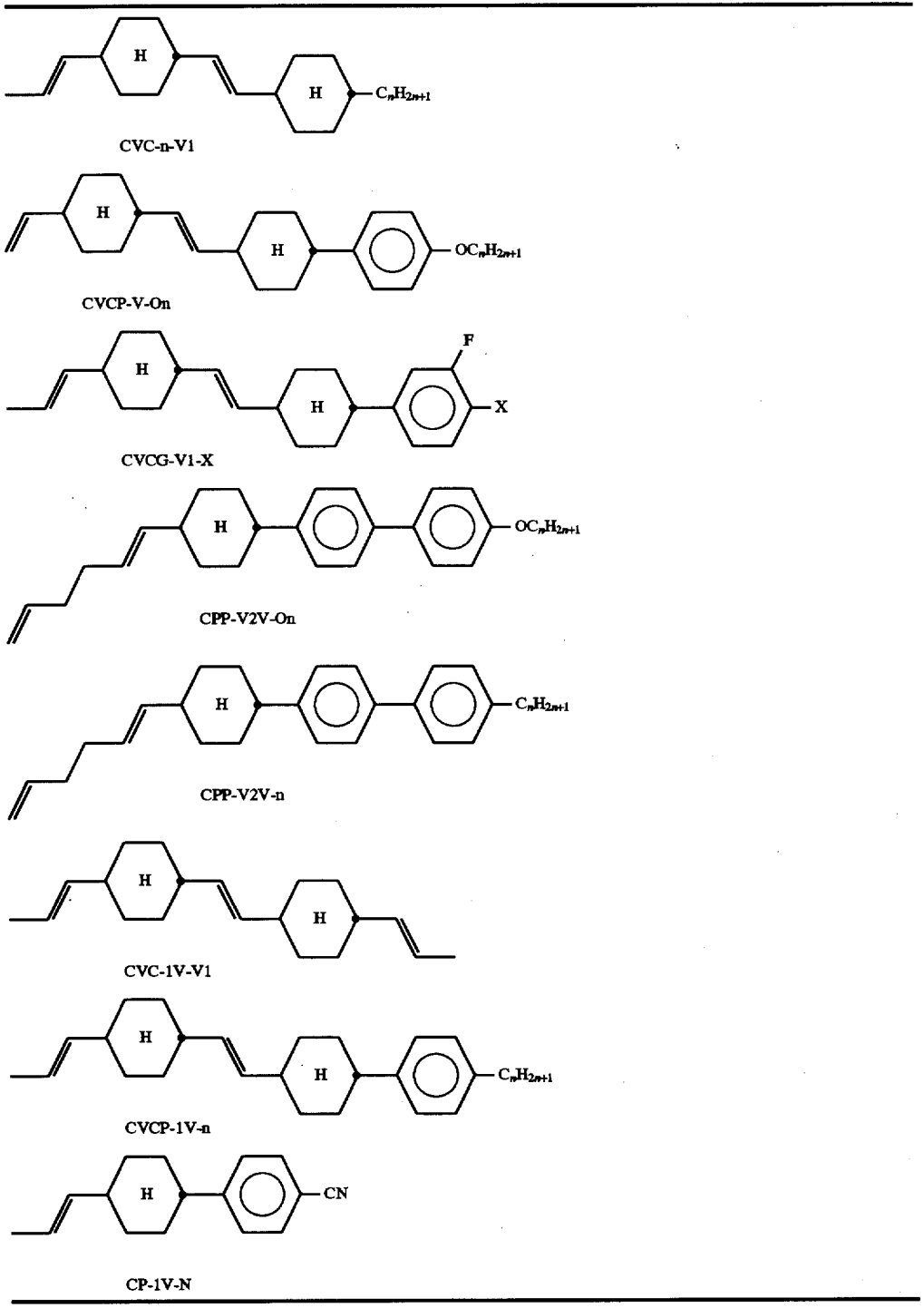

CVC-n-V1

CVCP-V-On

CVCG-V1-X

CPP-V2V-On

CPP-V2V-n

CVC-1V-V1

CVCP-1V-n

CP-1V-N

The examples below are intended to illustrate the invention without representing a limitation. m.p.=melting point, c.p.=clearing point. Above and below, percentages are by weight; the temperatures are given in degrees Celsius. "Conventional work-up" means that water is added, the mixture is extracted with dichloromethane or methyl tert-butyl ether. The organic phase is separated off, dried and evaporated, and the product is purified by crystallization and/or chromatography.

In addition, the following abbreviations are used:
C=crystalline solid state; S=smectic phase (the index denotes the phase type); N=nematic state; Ch=cholesteric phase; I=isotropic phase. The number between two symbols indicates the conversion temperature in degrees Celsius.
DAST Diethylaminosulphur trifluoride
DCC Dicyclohexylcarbodiimide DDQ Dichlorodicyanobenzoquinone
DIBALH Diisobutylaluminium hydride
DMSO Dimethyl sulphoxide
POT Potassium tert-butoxide
THF Tetrahydrofuran
pTsOH p-toluenesulphonic acid

EXAMPLE 1

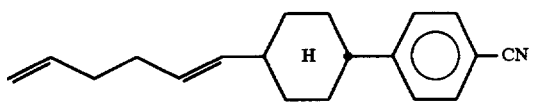

A suspension of 22 g of 4-pentenyltriphenylphosphonium bromide in 150 ml of THF is cooled to −10° C. 32.6 ml of BuLi solution (15% in n-hexane) and, after stirring for a further 15 minutes, trans-4-(p-cyanophenyl)cyclohexanecarbaldehyde dissolved in 50 ml of THF are added dropwise. After the reaction mixture has been stirred for a further 3 hours, it is warmed to room temperature and subjected to conventional work-up. The E/Z mixture (10.7 g) is dissolved in 50 ml of toluene, 1.73 g of sodium benzenesulphinate and 16.2 ml of 1N hydrochloric acid are added, and the mixture is refluxed overnight. Conventional work-up gives the target product:

C 57 N 66.9 I; $\Delta n$=+0.143; $\Delta\varepsilon$=16.08

The target product has a significantly higher N—I clearing point compared with the monoene compounds from the prior art (cf. p. 2 of the description).

The following compounds are prepared analogously:

$C_nH_{2n+1}$—〔chain〕—H—〔ring〕—R

| n | R |  |
|---|---|---|
| 1 | CN | C 41 N 89.4 I; $\Delta n$ = +0.156; $\Delta\varepsilon$ = 15.13 |
| 2 | CN |  |
| 3 | CN |  |
| 4 | CN |  |
| 5 | CN |  |
| 0 | OCH3 | C 24 N 30.3 I; $\Delta n$ = +0.091; $\Delta\varepsilon$ = 0.49 |
| 1 | OCH3 |  |
| 2 | OCH3 |  |
| 3 | OCH3 |  |
| 4 | OCH3 |  |
| 5 | OCH3 |  |
| 0 | OCF3 |  |
| 1 | OCF3 |  |
| 2 | OCF3 |  |
| 3 | OCF3 |  |
| 4 | OCF3 |  |
| 5 | OCF3 |  |
| 0 | CH3 | C −10 N −17.5 I; $\Delta n$ = + 0.078; $\Delta\varepsilon$ = −1.03 |
| 1 | CH3 |  |
| 2 | CH3 |  |
| 3 | CH3 |  |
| 4 | CH3 |  |
| 5 | CH3 |  |

$C_nH_{2n+1}$—〔chain〕—H—H—$C_mH_{2m+1}$

| n | m |  |
|---|---|---|
| 0 | 1 |  |
| 0 | 2 |  |
| 0 | 3 | C ?−33 $S_B$ 81 N 86.8 I; $\Delta n$ = +0.055; $\Delta\varepsilon$ = −0.15 |
| 1 | 1 |  |
| 1 | 2 |  |
| 1 | 3 |  |

$C_nH_{2n+1}$—〔chain〕—H—A—〔ring with $L^1, L^2$〕—(O)$_s$—$C_mH_{2m+1}$

| n | A | $L^1$ | $L^2$ | s | m |  |
|---|---|---|---|---|---|---|
| 0 | — | H | H | 0 | 2 |  |
| 0 | — | H | H | 0 | 3 |  |
| 1 | — | H | H | 0 | 2 |  |
| 1 | — | H | H | 0 | 3 |  |
| 0 | — | H | H | 1 | 1 | C 24 N 30.3 I; $\Delta n$ = +0.091; $\Delta\varepsilon$ = −0.49 |
| 0 | — | H | H | 1 | 2 |  |
| 0 | — | H | H | 1 | 3 |  |
| 0 | H | H | H | 0 | 1 | C 22 $S_B$ 114 N 193.6 I; $\Delta n$ = +0.121; $\Delta\varepsilon$ = 0.86 |
| 0 | H | H | H | 0 | 2 |  |
| 0 | H | H | H | 0 | 3 |  |
| 1 | H | H | H | 0 | 1 |  |
| 1 | H | H | H | 0 | 2 |  |
| 1 | H | H | H | 0 | 3 |  |
| 0 | H | H | H | 1 | 1 | C 64 $S_B$ 132 N 222.4 I; $\Delta n$ = +0.128; $\Delta\varepsilon$ = 1.18 |
| 0 | H | H | H | 1 | 2 |  |
| 0 | H | H | H | 1 | 4 |  |

-continued $C_nH_{2n+1}$—〈H〉—A—[L¹,L²-phenyl]—(O)$_s$—$C_mH_{2m+1}$

| n | A | L¹ | L² | s | m | |
|---|---|----|----|---|---|---|
| 1 | 〈H〉 | H | H | 1 | 1 | |
| 1 | 〈H〉 | H | H | 1 | 2 | |
| 0 | 〈H〉 | F | H | 1 | 1 | |
| 0 | 〈H〉 | H | F | 1 | 1 | |
| 0 | 〈H〉 | H | H | 0 | 2 | |
| 1 | 〈H〉 | H | H | 0 | 2 | |
| 0 | 〈H〉 | H | H | 1 | 1 | |
| 0 | 〈H〉 | H | H | 1 | 2 | |
| 0 | 〈H〉 | F | H | 1 | 1 | |
| 0 | 〈H〉 | F | H | 1 | 2 | |
| 0 | 〈H〉 | H | F | 1 | 1 | |
| 0 | 〈H〉 | H | F | 1 | 2 | |
| 0 | 〈H〉 | H | H | 0 | 1 | C 99 $S_B$ 120 N $S_A$ 125 N 196.7 I; $\Delta n = +0.201$; $\Delta\epsilon = 2.37$ |
| 0 | 〈H〉 | H | H | 1 | 1 | C 84 $S_B$ 123 N 230.3 I; $\Delta n = +0.209$; $\Delta\epsilon = 1.73$ |

$C_nH_{2n+1}$—〈H〉—[phenyl]—X

| n | X | |
|---|---|---|
| 0 | CN | C 1 N 9.9 I; $\Delta n = +0.109$; $\Delta\epsilon = 15.08$ |
| 1 | CN | |
| 2 | CN | |
| 3 | CN | |
| 4 | CN | |
| 5 | CN | |
| 0 | OCH$_3$ | |
| 1 | OCH$_3$ | |
| 2 | OCH$_3$ | |
| 3 | OCH$_3$ | |
| 4 | OCH$_3$ | |
| 5 | OCH$_3$ | |
| 0 | OCF$_3$ | |
| 1 | OCF$_3$ | |
| 2 | OCF$_3$ | |
| 3 | OCF$_3$ | |
| 4 | OCF$_3$ | |
| 5 | OCF$_3$ | |
| 0 | F | |
| 1 | F | |
| 2 | F | |
| 3 | F | |
| 4 | F | |
| 5 | F | |

$C_nH_{2n+1}$—〈H〉—[L-phenyl]—[F,F-phenyl]—(F)$_s$

| n | L | s | |
|---|---|---|---|
| 0 | H | 0 | |
| 0 | H | 1 | C 37 N 81.7 I; $\Delta n = +0.146$; $\Delta\epsilon = 10.12$ |
| 0 | F | 0 | |
| 0 | F | 1 | |
| 1 | H | 0 | |
| 1 | H | 1 | C 56 N 104.5 I; $\Delta n = +0.163$; $\Delta\epsilon = 12.26$ |
| 1 | F | 0 | |
| 1 | F | 1 | |

$C_nH_{2n+1}$—〈H〉—〈H〉—[L-phenyl]—[F,F-phenyl]—(F)$_s$

| n | s |
|---|---|
| 0 | 0 |

-continued

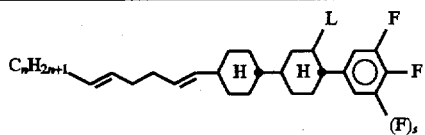

| n | s | |
|---|---|---|
| 0 | 1 | C 91 N 118.3 I; Δn = +0.088; Δε = 7.94 |
| 1 | 0 | |
| 1 | 1 | |

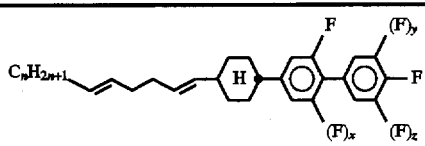

| n | x | y | z | R |
|---|---|---|---|---|
| 0 | 0 | 1 | 1 | F |
| 0 | 0 | 1 | 1 | OCF$_3$ |
| 0 | 0 | 1 | 1 | OCHFCF$_3$ |
| 0 | 1 | 1 | 1 | OCHFCF$_3$ |
| 0 | 0 | 1 | 1 | OCH$_2$CF$_3$ |
| 1 | 0 | 1 | 1 | F |
| 1 | 0 | 1 | 1 | OCF$_3$ |
| 1 | 0 | 1 | 1 | OCHFCF$_3$ |
| 1 | 1 | 1 | 1 | OCHFCF$_3$ |
| 1 | 0 | 1 | 1 | OCH$_2$CF$_3$ |

EXAMPLE 2

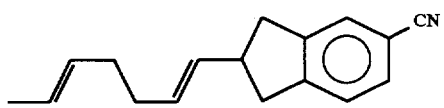

Step 2.1

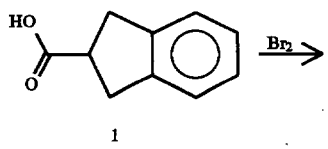

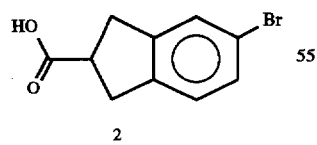

0.5 mol of bromine are added dropwise at 5° C. with stirring to 0.5 mol of 1 in CCl$_4$ and 1 g of iron powder. The mixture is stirred at 3° C. for a further 2 hours, stirred overnight, washed with sodium hydrogensulphite solution, water and 10% sodium hydroxide solution, and subjected to conventional work-up.

Step 2.2

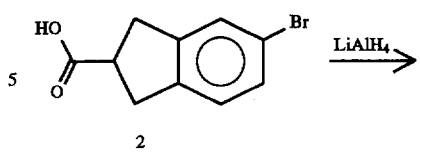

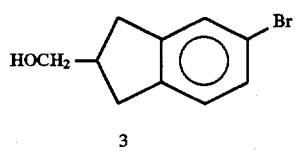

A solution of 0.035 mol of lithium aluminium hydride in 30 ml of toluene is added to 0.07 mol of 2 dissolved in 150 ml of THF. The mixture is refluxed for 1 hour and allowed to cool to room temperature, water is added, and the mixture is acidified with HCl and subjected to conventional work-up.

Step 2.3

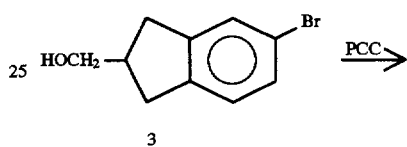

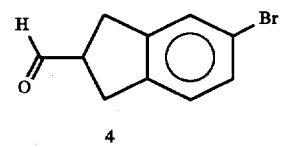

65.6 mmol of 3 are dissolved in 200 ml of dichloromethane, 79.6 mmol of pyridinium chlorochromate and 11 g of Celite are added, and the mixture is stirred at room temperature for 4 hours.

The reaction mixture is evaporated, and the residue is filtered through silica gel with methyl tert-butyl ether.

Step 2.4

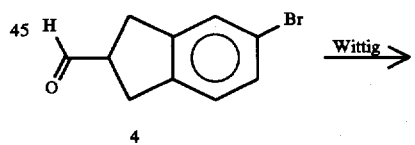

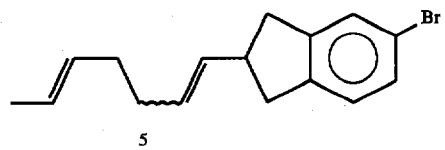

34 mmol of sodium bis(trimethylsilyl)amide (0.1 mol of solution in THF) are added dropwise to 91.4 mmol of 4-pentenyltriphenylphosphonium bromide in 50 ml of THF at 0° C. under a nitrogen atmosphere. The reaction mixture is stirred for a further 15 minutes, and 31.4 mmol of 4 dissolved in 50 ml of THF are added dropwise at −70° C. The mixture is allowed to warm to room temperature with stirring, water and sodium chloride solution are added, and the mixture is acidified using 2N hydrochloric acid and subjected to conventional work-up.

Step 2.5

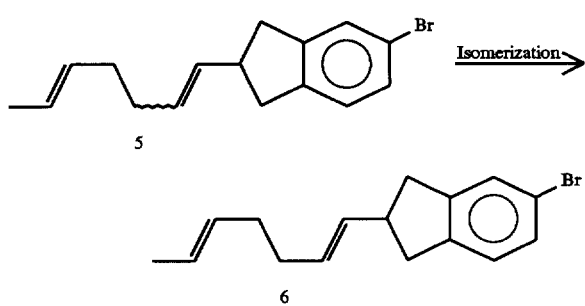

Under a nitrogen atmosphere, 23.3 mmol of 5 are dissolved in 30 ml of toluene and refluxed with 6.2 mmol of sodium benzenesulphinate and 8.5 ml of 1N hydrochloric acid. The mixture is subsequently subjected to conventional work-up.

Step 2.6

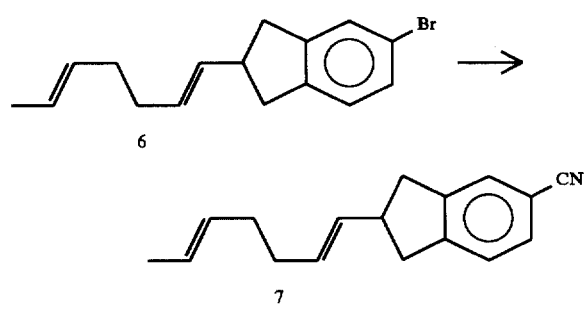

0.04 mol of 6 and 0.04 mol of CuCn in 400 ml of 1-methyl-2-pyrrolidone are stirred at 170° C. for 24 hours. The mixture is allowed to cool to room temperature and is subjected to conventional work-up.

MIXTURE EXAMPLES

Example A

| | | | |
|---|---|---|---|
| ME-5N.F | 5.0% | Clearing point [°C.]: | 87.9 |
| K6 | 9.0% | Δn [589 nm, 20° C.] | +0.1522 |
| K9 | 9.0% | $V_{90}/V_{10}$: | 1.024 |
| PCH-3 | 12.0% | | |
| PCH-301 | 13.0% | | |
| PCH-302 | 12.0% | | |
| CVCP-V-01 | 20.0% | | |
| CPP-V2V-1 | 10.0% | | |
| CPP-V2V-01 | 10.0% | | |

Example B

| | | | |
|---|---|---|---|
| K6 | 9.0% | Clearing point [°C.]: | 87.2 |
| K9 | 9.0% | Δn [589 nm, 20° C.] | +0.1424 |
| PCH-3 | 12.0% | $V_{90}/V_{10}$: | 1.045 |
| PCH-5 | 11.0% | | |
| BCH-32 | 7.0% | | |
| CCH-34 | 6.0% | | |
| CCH-35 | 6.0% | | |
| CVC-3-V1 | 20.0% | | |
| CPP-V2V-1 | 10.0% | | |
| CPP-V2V-01 | 10.0% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. Dienes of the formula I,

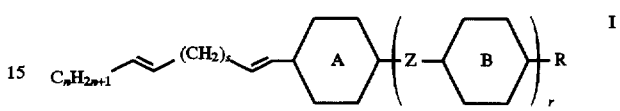

in which n is 0, 1, 2, 3, 4 or 5, r is 1, 2 or 3, s is 1 or 2,

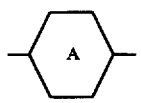

is trans-1,4-cyclohexylene or trans-1,3-dioxane-2,5-diyl,

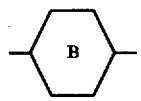

is trans-1,4-cyclohexylene, trans-1,3-dioxane-2,5-diyl, unfluorinated or mono- or polyfluorinated 1,4-phenylene, in which one or two CH groups may also be replaced by N, or the central part is

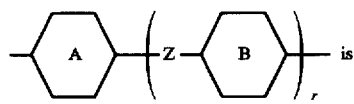

alternatively 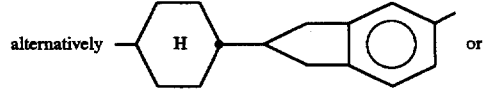 or

,

Z is a single bond, a bridging member selected from the group consisting of —CH$_2$CH$_2$—, —CH=CH—, —C≡C—, —CO—O—, —CH$_2$O—, —OCH$_2$— and —O—CO—, or any desired combination of two such bridging members, where two O atoms are not linked directly to one another, and R is —CN, —NCS, halogen or an alkyl, alkenyl, alkoxy or alkenyloxy group, in each case having up to 12 carbon atoms and in each case unsubstituted or monosubstituted or polysubstituted by fluorine, chlorine or both.

2. Dienes characterized by the sub-formula Ia

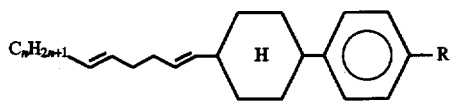

or sub-formula Ib

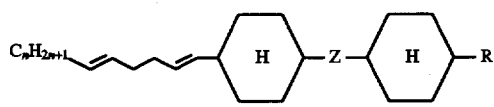

in which n, Z and R are as defined below:

n is 0, 1, 2, 3, 4 or 5,

R is —CN, —NCS, halogen or an alkyl, alkenyl, alkoxy or alkenyloxy group, in each case having up to 12 carbon atoms and in each case unsubstituted or substituted or polysubstituted by fluorine, chlorine or both; and Z is a single bond, a bridging member selected from the group consisting of —CH$_2$CH$_2$—, —CH=CH—, —C≡C—, —CO—O—, —CH$_2$O—, OCH$_2$— and —O—CO—, or any desired combination of two such bridging members, where two O atoms are not linked directly to one another.

3. Dienes, characterized by the sub-formula Ic,

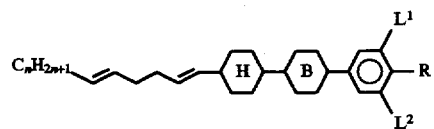

in which n,

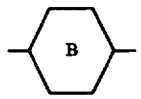

and R are as defined below:

n is 0, 1, 2, 3, 4 or 5,

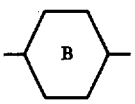

is trans-1,4-cyclohexylene or trans-1,3-dioxane-2,5-diyl, unfluorinated or mono- or polyfluorinated 1,4-phenylene, in which one or two CH groups may also be replaced by N, or the central part

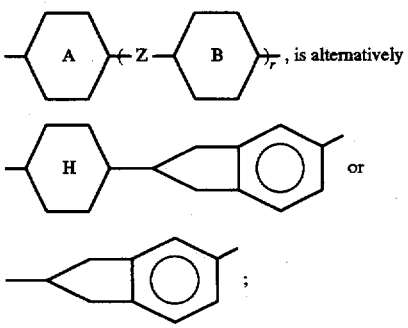, is alternatively and

R is —CN, —NCS, halogen or an alkyl, alkenyl, alkoxy group or alkenyloxy group, in each case having up to 12 carbon atoms and in each case unsubstituted or substituted or polysubstituted by fluorine, chlorine or both.

4. Dienes according to claim 3, characterized in that L$^1$=R=L$^2$=F.

5. A method of using the dienes of the formula I according to claim 1 which comprises incorporating a diene of formula I of claim 1 into a liquid crystalline media for electro-optical displays.

6. Liquid-crystalline media for electro-optical displays having at least two liquid-crystalline components, characterized in that at least one component is a diene of the formula I according to claim 1.

7. Electro-optical display based on a liquid-crystal cell, characterized in that the cell contains a medium according to claim 6.

* * * * *